US009062086B2

(12) United States Patent
Xie et al.

(10) Patent No.: US 9,062,086 B2
(45) Date of Patent: Jun. 23, 2015

(54) N-ACETYL L-CYSTEINE CHELATES AND METHODS FOR MAKING AND USING THE SAME

(71) Applicant: Viva Pharmaceutical, Inc., Richmond (CA)

(72) Inventors: Xueju Xie, Langley (CA); Rhett Sean Daniels, Fort Myers, FL (US); Patricia Gahan, Bonita Springs, FL (US)

(73) Assignee: Viva Pharmaceutical, Inc. (CA)

( * ) Notice: Subject to any disclaimer, the term of this patent is extended or adjusted under 35 U.S.C. 154(b) by 0 days.

(21) Appl. No.: 14/142,683

(22) Filed: Dec. 27, 2013

(65) Prior Publication Data

US 2015/0038577 A1    Feb. 5, 2015

Related U.S. Application Data

(63) Continuation of application No. 13/956,280, filed on Jul. 31, 2013.

(60) Provisional application No. 61/841,319, filed on Jul. 31, 2013.

(51) Int. Cl.
| | |
|---|---|
| *C07F 15/02* | (2006.01) |
| *C07F 1/08* | (2006.01) |
| *C07F 3/02* | (2006.01) |
| *C07F 3/06* | (2006.01) |
| *A23L 1/304* | (2006.01) |
| *A23L 1/305* | (2006.01) |

(52) U.S. Cl.
CPC ............... *C07F 15/025* (2013.01); *C07F 1/08* (2013.01); *C07F 3/02* (2013.01); *C07F 3/06* (2013.01); *A23L 1/3045* (2013.01); *A23L 1/3051* (2013.01)

(58) Field of Classification Search
CPC ............ C07F 15/025; C07F 3/06; C07F 3/02; C07F 1/08
USPC .......... 514/494, 499, 502, 562; 556/116, 134, 556/148; 562/557
See application file for complete search history.

(56) References Cited

U.S. PATENT DOCUMENTS

| | | | | |
|---|---|---|---|---|
| 3,749,770 | A * | 7/1973 | Martin ......................... | 424/70.4 |
| 4,927,808 | A * | 5/1990 | Kitahara et al. ............. | 514/15.4 |
| 6,429,219 | B1 | 8/2002 | Pearson et al. | |
| 6,531,608 | B2 | 3/2003 | Pearson et al. | |
| 8,067,628 | B2 * | 11/2011 | Sanina et al. ................ | 556/146 |
| 8,071,542 | B2 | 12/2011 | Connor et al. | |
| 2002/0151533 | A1* | 10/2002 | Pearson et al. ............... | 514/184 |
| 2005/0226942 | A1* | 10/2005 | Myhill et al. ................ | 424/725 |

FOREIGN PATENT DOCUMENTS

EP    0486921    5/1992

OTHER PUBLICATIONS

Yusuke Adachi, et al, Antidiabetic Zinc(II)-N-Acetyl-L-Cysteine Complex: Evaluations of in vitro Insulinomimetic and in vivo Blood Glucose-Lowering Activities, 29 Biofactors 213 (2007).*
Akira Hanaki, et al, Ternary Cu(II) Complexes, Cu(H_1 L)(ACys-) and Cu(H_2L)( ACys-); L=Peptides, ACys-=N-acetylcysteinate. Analogous Complexes to the Intermediates in the Transport of Cu(II) from Cu(H_2L) to Cysteine, 100 J Inorg. Biochem. 305 (2006).*
Harden, et al.; "A Randomized Controlled Pilot Trial of Oral N-Acetylcysteine in Children with Austism", Biol Psychiatry 2012; 71:956-961, 6 pgs.
Eby, et al.; "Rapid recovery from major depression using magnesium treatment", Medical Hyposotheses, George Eby Research, 14909-C Fitzhugh Road, Austin, TX 78736, United States ; Jan. 20, 2006, 9 pgs.
Giustarini, et al.; "N-Acetylcysteine ethyl ester (NACET): A novel lipophilic cell-permeable cysteine derivative with an unusual pharmacokinetic feature and remarkable antioxidant potential", Biochemical Pharmacology 84 (2012) 1522-1533; 12 pgs.
Banks, William A.; "Drug delivery to the brain in Alzheimer's disease: Consideration of the blood-brain barrier", Advanced Drug Delivery Reviews 64 (2012) 629-639, 11 pgs.
Goldstein, et al.; "The chemistry and biological activities of N-acetylcysteine", BBA—General Subjects, Apr. 15, 2013, 65 pgs.
Penugonda, et al.; "Comparative evaluation of N-acetylcysteine (NAC) and N-acetylcysteine amide (NACA) on glutamate and lead-induced toxicity in CD-1 mice", Toxicology Letters 201 (2011) 1-7, 7 pgs.
Arakawa, et al.; "N-acetylcysteine and neurodegenerative diseases: Basic and clinical pharmacology", The Cerebellum. 2007; 6: 308-314, 7 pgs.
Erickson, Michelle A.; "Inflammation-induced dysfunction of the low-density lipoprotein receptor-related protein-1 at the blood-brain barrier: Protection by the antioxidant N-acetylcysteine", Brain, Behavior, and Immunity 26 (2012) 1085-1094, 10 pgs.
Ghersi-Egea, et al.; "Brain protection at the blood-cerebrospinal fluid interface involves a glutathione-dependent metabolic barrier mechanism", Journal of Cerebral Blood Flow & Metabolism (2006) 26, 1165-1175, 11 pgs.
Farr, et al.; "The antioxidants a-lipoic acid and N-acetylcysteine reverse memory impairment and brain oxidative stress in aged SAMP8 mice", Journal ofNeur ochemistry, 2003, 84, 1173-1183, 11 pgs.

(Continued)

Primary Examiner — Sean Basquill
(74) Attorney, Agent, or Firm — Brett B. Bartel

(57) ABSTRACT

A nutritional supplement for a human, the supplement having a chelate comprised of an N-acetyl-L-cysteine ligand bonded to a metal to form a chelate ring. A method for preparing a chelate comprised of N-acetyl-L-cysteine ligand and a metal having the steps of: dissolving an amount of N-acetyl-L-cysteine in an aqueous solution, adding a metal to the aqueous solution, stifling and heating the aqueous solution, and removing the solvent under reduced pressure. A method of treating a human for one or more of oxidative stress, cardiovascular disease, cerebrovascular disease, neurodegenerative diseases, Alzheimer's disease, ADHD, bipolar, schizophrenia, autism, dementia, and HIV in a human comprising administering an effective amount of a composition having N-acetyl-L-cysteine in a chelate formation with a metal. A compound having a chelate formulation with a metal being chelated by an N-acetyl-L-cysteine ligand.

20 Claims, 7 Drawing Sheets

(56) References Cited

OTHER PUBLICATIONS

Neuwelt, et al.; "Therapeutic Efficacy of Aortic Administration of N-Acetylcysteine as a Chemoprotectant against Bone Marrow Toxicity after Intracarotid Administration of Alkylators, with or without Glutathione Depletion in a Rat Model", Cancer Res 2001;61:7868-7874., 8 pgs.

Viva Pharmaceutical, Inc.; International Search Report and Written Opinion for serial No. PCT/US13/53440, filed Aug. 2, 2013, mailed Dec. 20, 2013, 4 pgs.

Yukio Sugiura,et al.; "Iron-sulfide chelates of some sulfur-containing peptides as model complex of non-heme iron proteins, Biochemical and Biophysical Research Communications", vol. 46, Issue 2, Jan. 31, 1972, pp. 335-340, Abstract, 1 pg.

Erin E. Battin, et al.; "Antioxidant Activity of Sulfur and Selenium: A Review of Reactive Oxygen Species Scavenging, Glutathione Peroxidase, and Metal-Binding Antioxidant Mechanisms", Cell Biochem Biophys (2009) 55:1223, p. 4, right column, lines 8-9 from the bottom, 23 pgs.

\* cited by examiner

N-ACETYL L-CYSTEINE CHELATES AND METHODS FOR MAKING AND USING THE SAME

CROSS-REFERENCE TO RELATED APPLICATION

This application is a continuation of U.S. application Ser. No. 13/956,280 filed on Jul. 31, 2013, which is hereby incorporated by reference in its entirety, and which claimed priority based on U.S. Provisional Patent Application Ser. No. 61/841,319 filed Jun. 29, 2013.

FIELD

The present disclosure generally relates to chelated compounds with an N-acetyl L-cysteine ligand that is chelated with a metal.

BACKGROUND

N-acetyl-L-cysteine is a compound that is used for various nutritional, pharmaceutical, and medicinal purposes. It is able to cross the blood brain barrier and is a precursor of glutathione. Additionally, many minerals such as iron, magnesium, zinc, copper, calcium, and others are also used to supplement nutrition and treat medical conditions.

SUMMARY

A nutritional supplement for a human has a chelate made of an N-acetyl-L-cysteine ligand bonded to a metal to form a chelate ring.

A method for preparing a chelate amide of N-acetyl-L-cysteine ligand and a metal has the following steps: dissolving an amount of N-acetyl-L-cysteine in an aqueous solution, adding a metal to the aqueous solution, stifling and heating the aqueous solution, and removing the solvent under reduced pressure.

A method of treating a human for one or more of oxidative stress, cardiovascular disease, cerebrovascular disease, neurodegenerative diseases, Alzheimer's disease, ADHD, improved vision, bipolar, schizophrenia, autism, dementia, and HIV in a human by administering an effective amount of a composition having N-acetyl-L-cysteine in a chelate formation with a metal.

A compound has a chelate formulation with a metal being chelated by an N-acetyl-L-cysteine ligand.

DESCRIPTION OF THE FIGURES

The features and components of the following figures are illustrated to emphasize the general principles of the present disclosure and are not necessarily drawn to scale. Corresponding features and components throughout the figures may be designated by matching reference characters for the sake of consistency and clarity.

DETAILED DESCRIPTION

Figure 1:
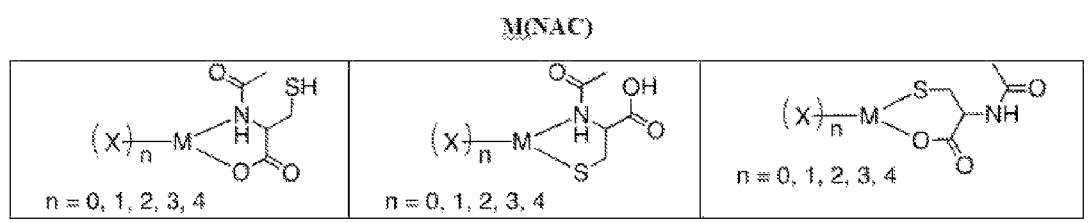
FIG. 1 is an NAC chelate with a mineral, where the molar ratio is 1:1.

The present disclosure will now be described more fully hereinafter with reference to the accompanying drawings, in which some, but not all embodiments of the disclosure are shown. Indeed this disclosure may be embodied in many different forms and should not be construed as limited to the embodiments set forth hereinafter; rather, these embodiments are provided so that this disclosure will satisfy applicable legal requirements. Like numbers refer to like elements throughout.

N-acetyl-L-cysteine

N-acetyl-L-cysteine is the acetylated precursor of the amino acid L-cysteine and is also known as N-acetyl cysteine, N-acetyl-L-cysteine or NAC. NAC is a derivative of cysteine with an acetyl group attached to its nitrogen atom and like most thiols (RSH) can be oxidized by a large variety of radicals and also serve as a nucleophile (electron pair donor).

NAC is a metal binding compound, as is the case with other thiols, having two potential coordination sites at the thiol and carboxyl groups where the latter is deprotonated at neutral pH. NAC is capable of binding transition metal ions, such as Zn(II), Mg(II) and Fe(III), and heavy metal ions such as Cd(II), Hg(II), and Pb(II) primarily through its thiol side chain and others. Thus, by chelating toxic metal ions NAC forms complex structures, which are readily excreted from the body removing them from intracellular or extracellular spaces.

NAC has been shown to exert survival-promoting effects in several cell systems. Cysteine is transported mainly by the alanine-serine-cysteine (ASC) system, a ubiquitous system of Na+-dependent neutral amino acid transport, in a variety of cells. NAC is a membrane-permeable cysteine precursor that does not require active transport and delivers cysteine to the cell in a unique way.

After free NAC enters a cell, it is rapidly hydrolyzed to release cysteine, a precursor of glutathione (GSH). GSH is synthesized intracellularly by the consecutive actions of c-glutamylcysteine synthetase and GSH synthetase. The synthesis of GSH is limited by the availability of substrates; cysteine is usually the limiting precursor. c-Glutamylcysteine synthetase is inhibited by feedback from GSH (Ki about 1.5 mM). Thus, under physiological conditions, this enzyme is probably not operating at its maximal rate. In addition, intracellular GSH is maintained in its thiol form by glutathione reductase, which requires NADPH. GSH participates nonenzymatically and enzymatically (GSH S-transferases (GSTs)) in protection against toxic compounds. Perhaps one of its most important functions is protection against oxidative damage caused by reactive oxygen species (ROS), many of which are generated during normal metabolism. In addition, GSH can react nonenzymatically with ROS and GSH peroxidase (and non-selenium (Se) peroxidase) to catalyze the destruction of hydrogen peroxide and hydroperoxides. Thus, NAC is an antioxidant and a free radical scavenging agent that increases intracellular GSH, a major component of the pathways by which cells are protected from oxidative stress.

NAC has been shown to interact with various metabolic pathways including, but not limited to, regulation of cell cycle and apoptosis; carcinogenesis and tumor progression;

mutagenesis; gene expression and signal transduction; immune-modulation; cytoskeleton and trafficking; and mitochondrial functions.

Oxidative stress has been shown to play a pivotal role in neuronal dysfunction and death in various neurodegenerative diseases, including sickle cell disease (SCD), myoclonus epilepsy of the Unverricht-Lundborg type, Alzheimer's disease, Parkinson's disease, tardive dyskinesia, and Down's syndrome. Free radical damage from oxidative stress has long been thought to play an important role in age-related neurodegenerative disorders. It has been suggested that free radical damage compromises composition integrity of cell membranes, which decreases membrane fluidity.

Oxidative stress can in some cases result in cognitive impairments. Antioxidants have been found to both prevent, treat, and reverse learning and memory deficits induced by free radicals. NAC is an antioxidant used to combat oxidative stress-induced damage. Studies have shown that NAC protects against oxidative stress in peripheral tissues and in the central nervous system. Additionally, it has been found to reverse age-related impairments in memory.

Redox exchange reactions between NAC and cysteine proteins in the plasma produce NAC-cysteine, NAC-NAC and cysteine. The latter can cross the epithelial cell membrane and sustain the synthesis of glutathione (GSH), which is the ubiquitous source of the thiol pool in the body and an important antioxidant involved in numerous physiological processes. These include detoxification of electrophilic xenobiotics, modulation of redox regulated signal transduction, regulation of immune response, prostaglandin and leukotriene metabolism, antioxidant defense, neurotransmitter signaling and modulation of cell proliferation (for a review). The synthesis of GSH is tightly regulated at various levels and is kept at the mM concentration range. Hence, the notion that the physiologic functions and therapeutic effects of NAC are largely associated with maintaining the levels of intracellular GSH is reasonable, and it is often difficult to discern the direct effect of NAC from those related to GSH.

The therapeutic use of antioxidants depends also on their ability to cross the cell membrane and those designed as neuroprotective treatment in acute or chronic neurological disorders should readily cross the blood-brain barrier (BBB). NAC has been shown to cross the BBB and can accumulate in the brain treating and reversing memory impairment. By increasing levels of brain cysteine, NAC is able to modulate glutamatergic and dopaminergic pathways. Studies have shown that NAC can influence a reduction in synaptic release of glutamate and an increase in dopamine release.

NAC has been in clinical practice for several decades. NAC is pharmaceutically available either intravenously, orally, or by inhalation. NAC has been used as a mucolytic agent and for the treatment of numerous disorders such as acetaminophen (paracetamol) intoxication, doxorubicininduced cardiotoxicity, stable angina pectoris, ischemia-reperfusion cardiac injury, acute respiratory distress syndrome, bronchitis, chemotherapy-induced toxicity, HIV/AIDS, radio-contrast-induced nephropathy, heavy metal toxicity and psychiatric disorders including schizophrenia, bipolar disorder, and addiction.

Overwhelming data supports the immuno-modulatory activity of NAC. Clinically, NAC improved the ocular symptoms of subjects with Sjogren's syndrome, cerebrovascular disease, enhanced natural killer and T-cell function, and delayed the reduction in CD4+ levels in HIV patients. Administration of NAC to post-menopausal women improved immune functions as exhibited by enhanced phagocytic capacity, leukocytes chemotaxis, natural killer function, and decreased TNF- and interleukin-8 (IL-8) levels. NAC was also proven beneficial in patients with the autoimmune disorder systematic lupus erythematosus (SLE).

NAC has a diversity of applications in both an experimental setting, as a tool for studies of oxidative stress induced by various agents including HNE, and in a clinical setting, as a therapeutic agent against several neurodegenerative diseases sharing primary or secondary mitochondrial defects that result in ROS overproduction and/or mitochondria-associated apoptosis. As a drug, NAC represents perhaps the ideal xenobiotic, that is, it is capable of directly entering endogenous biochemical processes as a result of its own metabolism.

Since NAC may cross the BBB, it is hoped that the experience gained with this unique agent will help in future efforts to design antioxidants and chemoprotective principles that are able to more accurately utilize endogenous biochemical processes for therapy of neurodegenerative diseases.

Abnormalities in the glutamatergic pathways may cause a number of complications. An imbalance in the excitatory/inhibitory systems with abnormalities in the glutamatergic pathways has been implicated in the pathophysiology of autism. Furthermore, chronic redox imbalance was also recently linked to autism. It has been shown that using oral N-acetylcysteine (NAC), a glutamatergic modulator and an antioxidant, in the treatment of behavioral disturbance in children with ADHD and autism.

NAC Derivatives

Derivatives of NAC also have many biological properties and aid in maintaining proper biological functions. Some of these derivatives include: N-acetyl-L-cysteine amide, N-acetyl-L-cysteine methyl ester, N-acetyl-L-cysteine ethyl ester, N-acetyl-L-cysteine propyl ester, and N-acetyl-L-cysteine isopropyl ester.

NAC Ester (NACET) is the simplest cysteine derivative. The esterification of the carboxyl group to produce N-acetylcysteine ethyl ester increases the lipophilicity of NAC and greatly improves its pharmacokinetics. NACET has much higher bioavailability (around 60%) than NAC. NACET rapidly enters the cells, then is trapped, and transforms into NAC and Cysteine. NACET is found in the cells of different tissues, including brain as it is able to cross the blood-brain barrier.

NACET also provides a variety of protective antioxidant effects. NACET may be taken orally and helps increase glutathione. It can accumulate in human erythrocytes. NACET may also behave as a potent protector against hydroperoxide-induced oxidative damage.

N-acetylcysteine amide (NACA) is a derivative of NAC and has been synthesized to improve the lipophilicity, membrane permeability, and antioxidant property. Studies have demonstrated the blood-brain barrier permeability and therapeutic potentials of NACA in neurological disorders including Parkinson's disease, Alzheimer's disease, Multiple sclerosis, Tardive dyskinesia, and HIV-associated neurological disorders. Additionally, NACA displays protective effect against pulmonary inflammation and antibiotic-induced apoptosis. Ongoing research continues on the possible therapeutic properties of NACA and its generics in the management of pathologies associated with extracellular matrix degradation and oxidative stress-related inflammation.

NACA has superior bioavailability than NAC as well as a molecule to improve the endurance and resident time of bio-scaffolds and biomaterials. More than 800 reviews on NAC have been published. However, no comprehensive review is available on the therapeutic applications of NACA.

NACA supplementation may be used to reduce, prevent, or counteract oxidative stress and free radical oxidant formation and overproduction in cells and tissues, as well as to provide a new source of glutathione.

Some studies show that NACA ameliorates cellular damage and subsequent loss of vision. Treatment of human retinal pigment epithelial cells with NACA was shown to protect against oxidative stress-induced cellular injury and death. NACA acted mechanistically by scavenging existing reactive oxygen species while halting production of reactive oxygen species by reversing lipid peroxidation. Furthermore, NACA functioned by increasing the levels of reduced glutathione and the phase II detoxification enzyme glutathione peroxidase.

NACA protects against oxidative stress-induced retinal pigment epithelial and photoreceptor cell death. Providing NACA may treat and in rescue retinal function and prevent vision loss secondary to retinal degenerative diseases, including age-related macular degeneration.

Chelates Generally

Amino acid chelates represent a stable bonding agent that attaches to mineral molecules to aid absorption. When minerals are bound to amino acid chelates, they are carried along through the stomach and small intestine wall, where vitamins and minerals are absorbed into the bloodstream. Chelation defines a complex chemical process of electrically charged molecules in the digestive tract, which regulate how nutrients pass from the intestine into the bloodstream.

Essential minerals bound to amino acid chelates stand a better chance of retention by the body to support cell functioning. Different minerals perform various functions, including the creation of strong teeth and bones. Some minerals contribute to healthy muscles, hormone production, adequate blood supply, and enzyme health. The human body cannot produce minerals; they must be obtained through food or supplements.

When a diet lacks sufficient nutrients, or when minerals consumed through food are not readily absorbed, a deficiency might occur. Several factors could contribute to minimal amounts of iron, copper, zinc, calcium, potassium, or manganese in the diet. Poor farming techniques may deplete these vital sources from the soil, and fruits and vegetables may then contain sparse levels of these nutrients. Produce picked before it ripens also might affect mineral content in fruits and vegetables.

Digestion begins in the mouth, where saliva breaks up starches before a meal passes into the stomach. Acids and enzymes in the stomach continue transforming food, such as protein and some carbohydrates, into usable forms. Amino acid chelates keep mineral molecules from breaking apart in the stomach before they travel into the small intestine, where penetration takes place.

A complicated chemical process in the small intestine is where one important role of chelation begins. Amino acid chelates block mineral molecules from developing electrical ions with weak positive or negative charges, which maintains a zero status necessary for absorption. These static molecules are capable of attaching to the intestinal wall and passing into the bloodstream along with amino acids.

Typically, mineral-amino acid chelates are promoted for their ability to enhance mineral absorption. The mineral is absorbed intact (as an amino acid), and the chelate structure "protects" the mineral from unwanted interaction with dietary substances. For example, it is known that calcium interferes with dietary iron absorption. In the case of NAC-iron, enclosing the iron in the chelate structure may prevent the unwanted interaction.

Synthetic chelates usually attach to metals, such as copper, zinc, magnesium, calcium, and iron. Natural amino acid chelates bind to metallic and inorganic minerals, including calcium, phosphate, and potassium. Amino acid derivatives may also be used as a ligand for a chelate.

Another important factor for proper absorption of minerals involves the way the minerals interact with each other. Calcium, for example, might deplete stores of vitamin D and magnesium as it enters the bloodstream. A similar process might occur when iron is absorbed, decreasing the bioavailability of vitamin C, B vitamins, and copper. Some mineral supplements address these interactions by adding other vitamins and minerals to the primary supplement. Thus, when preparing a formulation for a nutritional supplement comprising a metal chelate, it is very important to keep in mind the different interactions of the different vitamins and minerals, so that the supplement is not causing unwanted interactions and defeating the nutritional supplementation.

There a number of ways chelate has been defined. For the purposes of this disclosure, a chelate is an organic chemical that form two or more coordination bonds with a central metal ion. Heterocyclic rings are formed with the central metal atom as part of the ring. Some biological systems form metal chelates, e.g., the iron-binding porphyrin group of hemoglobin and the magnesium-binding chlorophyll of plants.

The National Nutritional Foods Association (NNFA) adopted a similar definition in 1996, specifically to establish a standard for chelated minerals using amino acids as the organic binding agents: "Metal Amino Acid Chelate is the product resulting from the reaction of a metal ion from a soluble metal salt with amino acids with a mole ratio of one mole of metal to one to three (preferably two) moles of amino acids to form coordinate covalent bonds." NAC chelates are consistent with this description, however, NAC chelates are also known to have a 4:1 ratio with the metal.

Mineral amino acid chelates, including derivative amino acid chelates, usually do not dissociate into free mineral ions in the stomach or intestine, preventing interactions with inhibitory dietary ligands and binding agents such as phytate and oxalate. Also, an undissociated compound may be less likely to cause gastrointestinal irritation in sensitive people.

Mineral amino acid chelates, including derivative amino acid chelates, are often absorbed intact by amino acid absorption pathways, which allow higher percentages of absorption than the usual mineral absorption pathways.

In addition to enhance mineral absorption, NAC-metal chelates are also intended to deliver, in addition to the mineral/metal moiety, a NAC moiety. In other words, a NAC-metal chelate aims to increase levels of both the mineral/mineral and NAC. Other mineral amino acid chelates that are used in nutritional supplements are exclusively focused on delivering the mineral. The amino acid ligand is chosen based primarily on factors that affect mineral delivery (and arguably, manufacturing ease, price) while disregarding the metabolic activity of the amino acid.

In the area of animal nutrition, one advantage of using these chelates over oxides or sulfate is that the NAC-metal chelates of the present disclosure are regarded as organic. In order to be absorbed, inorganic metal compounds must first dissolve in the stomach or intestines and the metal must complex with an organic compound in the gastrointestinal tract before it can be absorbed. If there are not enough of these organic complexing compounds present in the gastrointestinal tract in sufficient concentrations, adequate absorption of metal may not occur, despite the presence of an abundance of oxides, sulfates, or other inorganic metal compounds.

NAC is an ideal amino acid derivative because of its known role as a precursor to the major body antioxidant, glutathione. NAC has been shown in some studies to cross the blood brain barrier, which is important for brain glutathione synthesis. In situations of oxidative stress, glutathione and its precursors are used to restore oxidative balance. However, due to oral glutathione's poor bioavailability, NAC is often preferred.

Iron

Most living things need iron to survive and thrive. This mineral is vital for healthy red blood cells in people and animals, and plants need iron to produce chlorophyll, which is vital for healthy cell function and gives the plant its green color. Iron is a crucial component of hemoglobin, which is necessary to transport oxygen throughout the body.

Iron deficiency, also known as anemia, can cause fatigue, dizziness and shortness of breath. When dietary sources don't provide enough iron, a supplement may be needed for optimum health.

Iron supplements are most often used for certain types of anemia. Anemia is a low level of red blood cells that can cause fatigue and other symptoms. There's good evidence that iron supplements can treat anemia caused by: pregnancy, heavy menstrual periods, kidney disease, and chemotherapy. Some evidence also supports that iron supplements may be used for other types of anemia as well. Iron supplements are commonly recommended for infants and toddlers, teenage girls, and women who are pregnant or of childbearing age.

Iron supplements have also been used for treatment of ADHD.

The recommended dietary allowance includes the iron you get from both the food you eat and any supplements you take. The RDA for children 7-12 months old is 11 mg/day; 1-3 years is 7 mg/day; 4-8 years old 10 mg/day; 9-13 years old 8 mg/day. The RDA for females 14-18 years old is 15 mg/day; 19-50 years old is 18 mg/day; 51 years and older is 8 mg/day; pregnant is 27 mg/day; breastfeeding, under 19 years old, is 10 mg/day and over 19 years old is 9 mg/day. The RDA for males 14-18 years old is 11 mg/day and 19 and up is 8 mg/day.

The American Academy of Pediatrics suggests that starting at 4 months of age, breast fed infants should be supplemented with 1 mg/kg per day of oral iron. This should continue until iron-containing complementary foods, such as iron-fortified cereals, are introduced in the diet.

Additionally, beginning at 4 months of age, partially breastfed infants (more than half of their daily feedings as human milk) who are not receiving iron-containing complementary foods should receive 1 mg/kg per day of supplemental iron.

For most people, a good diet provides enough iron. Natural food sources of iron include: meat, fish, and poultry; vegetables, like spinach, kale, and broccoli; dried fruits and nuts. beans, lentils, and peas.

Chelated iron has undergone a process that binds it together with amino acids. This process makes the iron more similar to iron that occurs naturally in foods. Some studies show that the process of chelation makes the iron more easily absorbed through cell walls. NAC-iron chelate is simply iron that has undergone chelation, a chemical process that firmly binds the iron molecule to NAC.

Chelation forms a more stable ring-shaped molecule that is easier for plants and animals to absorb. Iron from dietary sources is bound to amino acids naturally, and chelation attempts to make supplemental iron more similar to these naturally occurring sources. Cells have membranes that allow some substances to pass through, while blocking others. NAC-iron chelate is disguised as an amino acid and is more passes through the cell membrane more easily, allowing the iron inside the cell where it is needed.

There are many nutritional benefits of using and NAC-iron chelate. Glutathione has an important role in iron metabolism. For example, red blood cells from iron-deficient children were shown to have decreased levels of reduced glutathione. This indicates that there is increased oxidative stress on the cells, which may lead to shortened life span of erythrocytes. NAC-iron chelate increases hemoglobin in the blood and offers hematinic benefits.

The iron of the NAC-iron chelate may be provided by one of many iron sources such as iron sulfate, iron oxide, iron chloride, iron acetate, iron hydroxide, iron fumurate, iron gluconate, iron lactate, carbonyl iron, and combinations thereof, though other sources may be used as known by those skilled in the art.

Zinc

Zinc is an essential mineral that is found in almost every cell. It has antioxidant effects and is vital to the body's resistance to infection. Zinc is also important for tissue repair. The body uses zinc in enzyme activities that produce DNA and RNA, regulate immune system functions and repair cells. Zinc is also necessary in trace amounts for reproduction and growth and the senses of smell and taste. The recommended dietary allowances (RDA) provide safe daily amounts of zinc intake for adolescents and adults: for men and pregnant women, 15 mg; for women, 12 mg.

Zinc is found naturally in seafood, shellfish, beef and other red meats, nuts and seeds, legumes and beans, whole grains, and dairy including milk and cheese. Tea, coffee, and certain medications may interfere with zinc absorption in the intestines.

Zinc is needed for the proper growth and maintenance of the human body. It is found in several systems and biological reactions, and it is needed for immune function, wound healing, blood clotting, thyroid function, and much more.

Zinc plays a role in maintaining vision, and it is present in high concentrations in the eye. Zinc deficiency can alter vision, and severe deficiency can cause changes in the retina. Low zinc levels can be also associated with male infertility, sickle cell disease, HIV, major depression, and type 2 diabetes.

Zinc might also have effects against viruses. Zinc may decrease the ability of cold viruses to grow on or bind to the lining of the nasal cavity. It appears to lessen symptoms of the rhinovirus (common cold). In addition, there is some evidence that zinc has some antiviral activity against the herpes virus.

Low zinc also exacerbates the effects of stress on the body and accelerates aging. Additionally, adequate zinc is necessary for optimal physical performance, energy levels, and body composition. Zinc affects protein synthesis and is required for proper function of red and white blood cells. It is highly concentrated in our bones, the pancreas, kidneys, liver, and retina.

Zinc deficiency is not uncommon worldwide. Symptoms include slowed growth, low insulin levels, loss of appetite, irritability, generalized hair loss, rough and dry skin, slow wound healing, poor sense of taste and smell, diarrhea, and nausea. Moderate zinc deficiency is associated with disorders of the intestine which interfere with food absorption (malabsorption syndromes), alcoholism, chronic kidney failure, and chronic debilitating diseases. Zinc deficiency, if not treated, can often result in slowed wound repair, limited brain function, hair loss, diarrhea and skin lesions.

Taking a zinc supplement is a good way to prevent and treat zinc deficiency. If a person is not getting enough zinc in their diet, a supplement is needed since the body cannot produce zinc on its own.

Zinc is so important because it is found in every tissue in the body and is directly involved in cell division. It is a powerful antioxidant that helps to prevent cancer. Zinc is also directly involved in proper endocrine function and the maintenance of ideal hormone levels.

There are several types of zinc supplements. Some types of zinc supplements include: zinc sulfate (which can cause stomach irritation), amino acid chelates of zinc, zinc gluconate, topical zinc (used for some mild skin conditions and cold sores), zinc oxide (used in some sun block preparations and some creams).

Some zinc supplements have some serious side effects caused by too much zinc. Some of these side effects include: abdominal pain (usually due to the mode of absorption), nausea, fever, cough, diarrhea, drowsiness, vomiting, and restlessness. Many of these side effects are not found when zinc is chelated with NAC.

Zinc is an excellent antioxidant. Antioxidants get rid of free radicals that cause damage to cells in the body by bonding with them and neutralizing them. Zinc is particularly good at countering the damaging effect of high iron. Zinc also targets free radicals that cause inflammation and is especially effective at detoxifying heavy metals from the brain.

The super antioxidant effects of zinc allow it to efficiently remove toxins from the body and keep them from building up in tissue and causing damage. The progression of neurodegeneration and Alzheimer's disease is accelerated by heavy metal buildup in the brain. Zinc can help get rid of those toxins, and it also helps maintain cellular homeostasis of brain cells.

Zinc plays a key role in neurotransmitter function and helps to maintain brain structure and health. It is necessary in the metabolism of melatonin, which regulates dopamine. Also, zinc is part of an enzyme that is necessary for the anabolism of fatty acids in the brain membrane. This is very important because a key part of supporting brain health and function is to ensure the membrane gets the nutrients it needs.

A study has shown the effect of giving supplemental zinc improves spatial memory and overall cognitive development. The data supports that zinc can treat attention deficit hyperactivity disorder (ADHD), which indicates its importance.

Zinc is a commonly ignored mineral for treating ADHD. Studies show children with ADHD tend to have lower zinc than healthy children. One study of 400 children with diagnosed ADHD found that taking 150 mg/d of zinc improved impaired social behavior and made subjects less hyperactive and impulsive than a placebo. Subjects that had higher body mass index and lower fatty acid level had more dramatic improvements in socialization and hyperactivity measures from taking zinc.

Zinc can also be used to treat depression. The exact relationship between zinc deficiency and depression is unknown, however it likely has to do with the role of zinc in neurotransmitter and hormone production. Dopamine production, which is partly regulated by zinc status, is a chemical that boosts energy, mood, and reward-driven learning. Poor insulin health or low testosterone levels can lead to health problems that increase rates of depression and low energy. Zinc has great antioxidant power and has the ability to get rid of inflammatory biomarkers such as C-reactive protein and tumor necrosis factor, which causes cell damage. So zinc intake has been shown to be beneficial when treating depression.

Zinc deficiency may affect depression in women more than men. Women who were already using antidepressants may have low zinc levels and are five times more likely to have ongoing depression. The gender-based relationship between low zinc and depression may be related to how zinc influences energy levels and production of the hormone estrogen. In women, estrogen is involved in serotonin production—the neurotransmitter that makes influences pleasure—and zinc supplementation can increase the density of serotonin receptors in the brain.

Zinc chelate is a zinc ion that has been bonded to a ligand or organic compound—those containing carbon. The ligand bonds to a metal ion, in this case zinc, creating a complex molecule. In the case of zinc chelate, the organic compounds break down easily in the body allowing the zinc ion to be freely absorbed into the bloodstream.

NAC can form act as the ligand in a chelate with zinc just as other amino acids are known to be able to do. A NAC-zinc chelate is advantageous over other amino acids because many of the conditions that require zinc supplementation are additionally benefited from NAC supplementation. For example, cognitive function is improved by administering zinc and NAC.

Zinc availability affects brain glutathione. A deficit in zinc availability can increase cell oxidant production, affect the antioxidant defense system, and trigger oxidant-sensitive signals in neuronal cells. GSH levels can become low with zinc deficiency. γ-Glutamyl-cysteine synthetase (GCL), the first enzyme in the GSH synthetic pathway, may also be altered by zinc deficiency. The protein and mRNA levels of the GCL modifier and catalytic subunits may be lower in zinc deficient. The nuclear translocation of transcription factor nuclear factor (erythroid-derived 2)-like 2, which controls GCL transcription, may be impaired by zinc deficiency.

NAC-zinc chelate may be beneficial to the treatment of AIDS. Sufficient essential nutrients such as methionine, cysteine, copper, selenium, zinc and vitamins C and E are indispensable for the maintenance of optimal (immune) cell functions. The way in which the right amount of cysteine, glutathione (GSH), and copper and zinc ions are made available in the right place at the right time and in the right form can prevent an unchecked multiplication of (AIDS) viruses in a more passive or active way.

Zinc and copper ions stimulate/inhibit/block in a concentration-dependent way the (intracellular) activation of essential protein-splitting enzymes such as HIV proteases. Zinc and copper ions may act as 'passive' virus inhibitors. Apart from this, zinc ions directly or indirectly regulate, via zinc finger protein molecular structures, the activities of virus-combating Th-1 cells such as cytotoxic T-cells (CTLs). Zinc ions as regulators of the active, virus-combating Th-1 cells. Zinc and copper ions that remain available in sufficient amounts via cysteine/GSH are effective natural inhibitors/combaters of (AIDS) viruses and thereby prevent the development of chronic virus diseases that can lead to AIDS, autoimmune diseases, (food) allergies and/or cancer.

A safe, relatively inexpensive and extensively tested medicine such as N-acetylcysteine NAC can help in supplying extra cysteine. An NAC-Zn or NAC-Cu chelate would be even more beneficial in treating compromised immune functions.

The zinc of the NAC chelates may be provided by one of many zinc sources such as zinc sulfate, zinc oxide, zinc chloride, zinc acetate, zinc hydroxide, zinc gluconate, zinc citrate, zinc lactate, and combinations thereof, though other sources may be used as known by those skilled in the art.

Magnesium

Magnesium is an important mineral that is needed by every cell in the human body. About half of the magnesium stores in the body are found in the cells of the body's organs and tissues, and the other half is found in our bones where it occurs in combination with phosphorus and calcium. Magnesium is required by the body to carry out various biochemical functions such as enzyme activity. If one suffers from magnesium deficiency, it can lead to a myriad of conditions.

Magnesium is a vital nutrient that is often deficient in modern diets. Our ancient ancestors would have had a ready supply from organ meats, seafood, mineral water, and even swimming in the ocean, but many modern soils are depleted of minerals, and magnesium is removed from water during routine municipal treatment. The current RDA for adults is between 320 and 420 mg daily, and the average US intake is around 250 mg daily.

Magnesium plays an important role in biochemical reactions all over your body. It is involved in a lot of cell transport activities, in addition to helping cells make energy aerobically or anaerobically. Bones are a major reservoir for magnesium, and magnesium is the counter-ion for calcium and potassium in muscle cells, including the heart. If the body's magnesium is too low, it can experience muscle cramps, arrhythmias, and even sudden death. Ion regulation is important with respect to how muscles contract and nerves send signals. In the brain, potassium and sodium balance each other. In the heart and other muscles, magnesium pulls some of the load.

Magnesium also is designed to offset calcium. Magnesium is very important to bone health and balances out calcium to ensure a working body. Without magnesium, calcium can actually become toxic and affect your brain health.

Magnesium has been a home remedy for many ailments, including anxiety, apathy, depression, headaches, insecurity, irritability, restlessness, talkativeness, and sulkiness. One study showed that magnesium deficiency could cause depression, behavioral disturbances, headaches, muscle cramps, seizures, ataxia, psychosis, and irritability—all reversible with magnesium repletion.

Several studies have also looked how stress levels affect magnesium. They found that during periods of extreme stress, magnesium is often used up by the body.

That means that not only is a significant portion of the country magnesium deficient, potentially leading to anxiety—there may also be a high number of people that use up their magnesium reserves as a result of their anxiety, thus contributing to more anxiety and more stress.

Magnesium deficiency is also caused because magnesium is depleted excessively through the urine and gastrointestinal that leads to malabsorption of magnesium or excessive loss of magnesium in the stool.

Inadequate dietary intake of magnesium also may lead to different health conditions, including: loss of appetite, disorientation, confusion, psychotic behavior, depression, tremors, convulsions, numbness, tingling, and cramps in the muscles, vasodilation, or widening of the blood vessels, coronary spasms, abnormal heart rhythms, seizures, osteoporosis, cerebral infarction, irritability of the nervous system.

Magnesium deficiency is likely common in the United States. Some studies have shown that the diets of most of the adult population in America are deficient in magnesium, and it was also found that compared to Hispanics or non-Hispanic whites, the non-Hispanic black population consumed lower amounts of magnesium, and that people who were 70 years of age and above consumed less magnesium compared to younger adults.

Treatments that involve diuretics, certain medications used for treating cancer, and certain antibiotics, can lead to an increase of the loss of magnesium through urine. Diabetes that is not adequately controlled can result in magnesium being lost excessively in urine, resulting in depleted magnesium stores in the body. Alcohol also leads to magnesium being excreted excessively in the urine, and a high intake of alcohol has been linked to magnesium deficiency. Excessive or chronic diarrhea and vomiting can also lead to deficiency due to the depletion of the mineral. Some of the other possible causes of magnesium depletion in the body are: postoperative complications subsequent to bowel resection, parenteral fluids being administered without adding magnesium salts, and nasogastric suctioning; and malnutrition or starvation.

Loss of magnesium in excessive amounts can be the result of: diabetic acidosis and severe dehydration; hypoparathyroidism and hyperaldosteronism, resulting in hypocalcemia and hypokalemia; hypercalcemia and hyperthyroidism; adrenocortical hormones being released in excessive amounts. Magnesium deficiency can also be primarily due to genetic disorders.

The Recommended Dietary Allowance, or RDA for males is: 410 mg for ages 14 to 18; 400 mg for ages 19 to 30; 420 mg for ages 31 and above. The RDA for females is: 360 mg for ages 14 to 18; 310 mg for ages 19 to 30; 320 mg for ages 31 and above. During pregnancy the RDA is increased to 400 mg (for 14 to 18 years of age). For pregnant women aged 19 to 30, the RDA is 350 and for age above 31 years, it is 360.

Magnesium deficiency can be treated. If there is only a mild deficiency of magnesium, it can be restored to healthy levels by increasing the intake of magnesium in the diet. Adults at risk of magnesium deficiency can get their recommended amounts by consuming dark green leafy vegetables as well as at least five servings of vegetables and fruits every day. Rice, wheat bran, and oats are some of the grains that are high in magnesium.

Magnesium supplements can provide adequate nutrition, although some types, especially magnesium salts, can lead to diarrhea. Some health food outlets have magnesium oxide, which is a form of magnesium that is absorbed the least efficiently by the human body.

Chelated magnesium can provide better absorption than many magnesium salts currently used. This is because chelated minerals are better absorbed and readily disassociate.

Patients with HIV are known to have decreased glutathione and cysteine levels, and they are also known to have magnesium deficiency. Since NAC is the precursor to glutathione, an NAC-magnesium chelate is synergistically beneficial for an HIV patient.

Additionally, magnesium is an obligatory cofactor in glutathione synthesis. As a result, magnesium deficiency may impair glutathione synthesis. In addition, many neurodegenerative conditions have been reported to be associated with decreased brain magnesium levels and increased oxidative stress. A nutritional supplement providing a source of NAC-magnesium chelate can increase both brain magnesium and glutathione levels. Additionally, because NAC crosses the blood brain barrier, it would be an effective treatment for neurodegenerative conditions.

The magnesium of the NAC chelates may be provided by one of many magnesium sources such as magnesium sulfate, magnesium oxide, magnesium chloride, magnesium acetate, magnesium hydroxide, magnesium gluconate, magnesium fumarate, magnesium lactate, and combinations thereof, though other sources may be used as known by those skilled in the art.

Copper

Copper is an essential trace mineral that is present in all body tissues. It plays a role in the formation of healthy connective tissues (hair, skin, nails, tendons, ligaments and blood vessels) and in the normal functioning of muscles and the immune and nervous systems. The human body requires copper for normal growth and health. Copper, along with iron, is a critical component in the formation of red blood cells. Copper also influences the functioning of the heart and arteries. Copper is needed to help your body use iron. It is also important help the body use sugar. It is also part of the antioxidantenzyme, superoxide dismutase (SOD). Copper is needed to make adenosine triphosphate (ATP), the energy the body runs on. Synthesis of some hormones requires copper, as does the synthesis of collagen. In addition, the enzyme, tyrosinase, which plays a role in the production of skin pigment, requires copper to function.

Copper is found in many foods, particularly in organ meats, seafood, nuts, seeds, wheat bran cereals, grain products, and cocoa products. The human body mostly stores copper in the bones and muscles. The liver regulates the amount of copper that is in the blood. Copper is used as medicine. Copper supplements are used for treating copper deficiency and the anemia it may cause. While having too little copper (copper deficiency) is rare, it sometimes occurs in people who get too much zinc from diet or supplements, have intestinal bypass surgery, or are fed by feeding tubes. Malnourished infants can also have copper deficiency. Signs of deficiency include bleeding under the skin, damaged blood vessels, hair loss, pale skin, and an enlarged heart. Symptoms include fatigue and, because copper plays a role in immunity, imbalances can make you more susceptible to infections.

Copper supplementation may also used for improving wound healing, and treating osteoarthritis and brittle bones (osteoporosis).

According to the National Institutes of Health (NIH), the daily recommended amounts: for adults, 900 mcg; for pregnant women over age 18, 1,000 mcg; and for lactating women over age 18, 1,300 mcg. According to the NIH, the daily recommended amounts that a child needs are: for infants 0-6 months is 200 mcg, for infants 7-12 months, 220 mcg, for children 1-3 years, 340 mcg, for children 4-8 years, 440 mcg; for children 9-13 years, 700 mcg, and adolescents 14-18 years, 890 mcg.

Copper enters a human cell via the hCTR1 transporter and is then delivered to several copper chaperones, which subsequently transfer the metal to specific targets via protein:protein interactions. It is has been assumed that chaperones acquire copper directly from hCTR1. However, some reports have pointed to an intermediary role for glutathione (GSH), an abundant copper-binding tri-peptide. An NAC:Cu chelate would provide a synergistic relationship in proper glutathione synthesis, metabolism, and bioavailability.

NAC-copper chelate has advantages over other minerals to be used in nutritional supplements. Too much zinc can affect iron absorption. However, iron metabolism requires copper. High levels of zinc and iron can also have adverse effects. Calcium is known to disrupt iron absorption. Copper supplementation can correct for too much zinc and/or iron in the diet.

Glutathione is known to play a role in copper metabolism. Depletion of glutathione has shown to inhibit copper metabolism. NAC copper would then have synergistic affects on glutathione metabolism and copper metabolism.

NAC will also form chelates with other minerals such as molybdenum, chromium, and selenium.

Nutritional Supplements

A nutrition supplement or pharmaceutical preparation may include an NAC-metal chelate. Depending on the perpose of the nutrition supplement or pharmaceutical preparation, additional vitamins and minerals may also comprise the nutrition supplement or pharmaceutical preparation.

Additionally, fillers and/or drying agents including mineral oil, soy flour, wheat flour, rice flour, silica, maltodextrin, microcrystalline cellulose, and others may also be added to the nutritional supplements comprising chelates of the present disclosure. The dosage form can include one or more pharmaceutically acceptable excipients, flavorants, sweeteners, or some combination of these.

Pharmaceutically acceptable excipients which can be included in the nutritional supplement include, for example, tablet binders, acidifying agents, alkalinizing agents, adsorbents, preservatives, antioxidants, buffering agents, colorants, dispersants, thickeners, solubilizing agents, encapsulating agents, stiffening agents, tablet anti-adherents, tablet and capsule diluents, tablet coating agents, tablet direct compression excipients, tablet disintegrants, tablet glidants, tablet lubricants, tablet opaquants, and tablet polishing agents.

In one embodiment, the active ingredients of the NAC-metal chelate nutritional supplement are mixed with the one or more excipients and compressed to form a tablet. The tablet is then optionally coated with one or more coats, at least one of which preferably comprises a flavorant. In another embodiment, the NAC-metal chelate is used in a softgel.

Chelate Preparation

This disclosure also provides a method for preparing an NAC-metal chelate that may be used to supplement a person's nutrition. The method for preparing an NAC chelate involves reacting a metal with N-acetyl-L-cysteine in an aqueous solvent. NAC is added to an aqueous solvent and a metal is added to the solution and is dissolved. The metal may be provided from any of the following: ions, elemental, oxides, hydroxides, carbonates, bicarbonates, sulfates, nitrates, chlorides, phosphates, citrates, lactates, gluconates, fumurates, amino acid salts and combinations thereof. This list is only for example and is non limiting as those skilled in the art will know of additional metals.

The reaction is performed in an aqueous solvent, being water alone or a mixture of water and water miscible solvent. In one embodiment, the aqueous solvent is water alone. The proportion of water to water miscible solvent may depend on the kinetics and/or thermodynamics of the reaction. The reaction mixture may also optionally contain additional agents such as buffers, pH adjusters, and stabilizers. This mixture forms a colorless transparent solution with an acidic pH.

Then a mineral salt or a metal is added to the solution and the mixture is stirred and heated. The reaction may be performed at from room temperature to 100° C. In one embodiment, the reaction is performed at 75° C.

The reaction is allowed to proceed for a time sufficient to achieve substantial completion. Reference to substantial completion of the reaction is intended to refer to the substantial consumption (e.g. greater than 90%) of the of the NAC-metal ion. The time required to achieve substantial completion will vary and will depend on the temperature of the mixture.

The solvent should be removed under reduced pressure. Additionally, the solvent may be spray dried or freeze dried.

The structure of NAC-metal chelate may be confirmed by FT-IR through comparison of the stretching of bonds or shifting of absorption caused by bond formation.

EXAMPLES

The following examples illustrate the practical methods of making pure NAC-metal chelates of the present disclosure. It is to be understood these examples should not be considered as limitations of our disclosure, the experimental data of the examples is only for the illustration of producing the pure NAC-metal chelates and their characteristics as well.

Example 1

NAC-Iron Chelate (Fe:2NAC)

N-Acetyl-L-Cysteine (NAC, 16.4646 g, 100.8918 mmol) was dissolved in water (50 mL), forming a colorless transparent solution (pH 2). Iron(II) hydroxide, Fe(OH)2 (4.5330 g, 50.44 mmol) was added to the reaction. The mixture was stirred and heated at 75° C., until a colorless transparent solution was formed (pH 4). The solvent was removed under reduced pressure. Structure of NAC-iron chelate was confirmed by FT-IR through comparison of the stretching of bonds or shifting of absorption caused by bond formation. FT-IR (KBr, cm$^{-1}$): 1650-1550 (5-member ring, metal amino acid chelate). In this example, there are 2 NACs to each iron.

Example 2

NAC-Iron Chelate (Fe:3NAC)

N-Acetyl-L-Cysteine (NAC, 24.6968 g, 151.3376 mmol) was dissolved in water (50 mL), forming a colorless transparent solution (pH 2). Iron(II) hydroxide, Fe(OH)2 (4.5330 g, 50.44 mmol) was added to the reaction. The mixture was stirred and heated at 75° C., until a colorless transparent solution was formed (pH 4). The solvent was removed under reduced pressure. Structure of NAC-iron chelate was confirmed by FT-IR through comparison of the stretching of bonds or shifting of absorption caused by bond formation. FT-IR (KBr, cm$^{-1}$): 1650-1550 (5-member ring, metal amino acid chelate). In this example, there are 3 NACs to each iron.

Example 3

NAC-Magnesium Chelate (Mg:2NAC)

N-Acetyl-L-Cysteine (NAC, 9.1020 g, 55.7756 mmol) was dissolved in water (50 mL), forming a colorless transparent solution (pH 2). Magnesium oxide, (MgO, 1.1240 g, 27.9880 mmol) was added to the reaction, forming a white opaque solution. The mixture was stirred and heated at 75° C., until a colorless transparent solution was formed (pH 5). The solvent was removed under reduced pressure. Structure of NAC-magnesium chelate was confirmed by FT-IR through comparison of the stretching of bonds or shifting of absorption caused by bond formation. FT-IR (KBr, cm$^{-1}$): 1650-1550 (5-member ring, metal amino acid chelate). This example is about 7% magnesium and 93% NAC by dry weight. In this example, there are 2 NACs to each magnesium.

Example 4

NAC-Magnesium Chelate (Mg:3NAC)

N-Acetyl-L-Cysteine (NAC, 13.653 g, 83.6634 mmol) was dissolved in water (50 mL), forming a colorless transparent solution (pH 2). Magnesium oxide (MgO, 1.1240 g, 27.9880 mmol) was added to the reaction, forming a white opaque solution. The mixture was stirred and heated at 75° C., until a colorless transparent solution was formed (pH 3). The solvent was removed under reduced pressure. Structure of NAC-magnesium chelates was confirmed by FT-IR through comparison of the stretching of bonds or shifting of absorption caused by bond formation. FT-IR (KBr, cm$^{-1}$): 1650-1550 (5-member ring, metal amino acid chelate). In this example, there are 3 NACs to each magnesium.

Example 5

NAC-Magnesium Chelate (Mg:4NAC)

N-Acetyl-L-Cysteine (NAC, 18.2040 g, 111.5510 mmol) was dissolved in water (50 mL), forming a colorless transparent solution (pH 2). Magnesium oxide (MgO, 1.1240 g, 27.8877 mmol) was added to the reaction, forming a white opaque solution. The mixture was stirred and heated at 75° C., until a colorless transparent solution was formed (pH 3). The solvent was removed under reduced pressure. Structure of NAC-magnesium chelate was confirmed by FT-IR through comparison of the stretching of bonds or shifting of absorption caused by bond formation. FT-IR (KBr, cm$^{-1}$): 1650-1550 (5-member ring, metal amino acid chelate). In this example, there are 4 NACs to each magnesium.

Example 6

NAC-Zinc Chelate (Zn:1NAC)

N-Acetyl-L-Cysteine (NAC, 9.1542 g, 56.0952 mmol) was dissolved in water (100 mL), forming a colorless transparent solution (pH 2). Zinc oxide (ZnO, 4.5666 g, 56.0952 mmol) was added to the reaction, forming a white translucent solution. The mixture was stirred and heated at 75° C., until a colorless transparent solution was formed (pH 5). The solvent was removed under reduced pressure. Structure of NAC-zinc chelate was confirmed by FT-IR through comparison of the stretching of bonds or shifting of absorption caused by bond formation. FT-IR (KBr, cm$^{-1}$): 1650-1550 (5-member ring, metal amino acid chelate). In this example, there are 1 NACs to each zinc.

Example 7

NAC-Copper Chelate (Cu:1NAC)

N-Acetyl-L-Cysteine (NAC, 3.3454 g, 20.500 mmol) was dissolved in water (100 mL), forming a colorless transparent solution (pH 2). Cupper hydroxide (Cu(OH)$_2$, 2.00 g, 20.500 mmol) was added to the reaction. The mixture was stirred and heated at 75° C., until a colorless transparent solution was formed (pH 4). The solvent was removed under reduced pressure. Structure of NAC-copper chelate was confirmed by FT-IR through comparison of the stretching of bonds or shifting of absorption caused by bond formation. FT-IR (KBr, cm$^{-1}$): 1650-1550 (5-member ring, metal amino acid chelate). In this example, there are 1 NACs to each copper.

Figure 2:
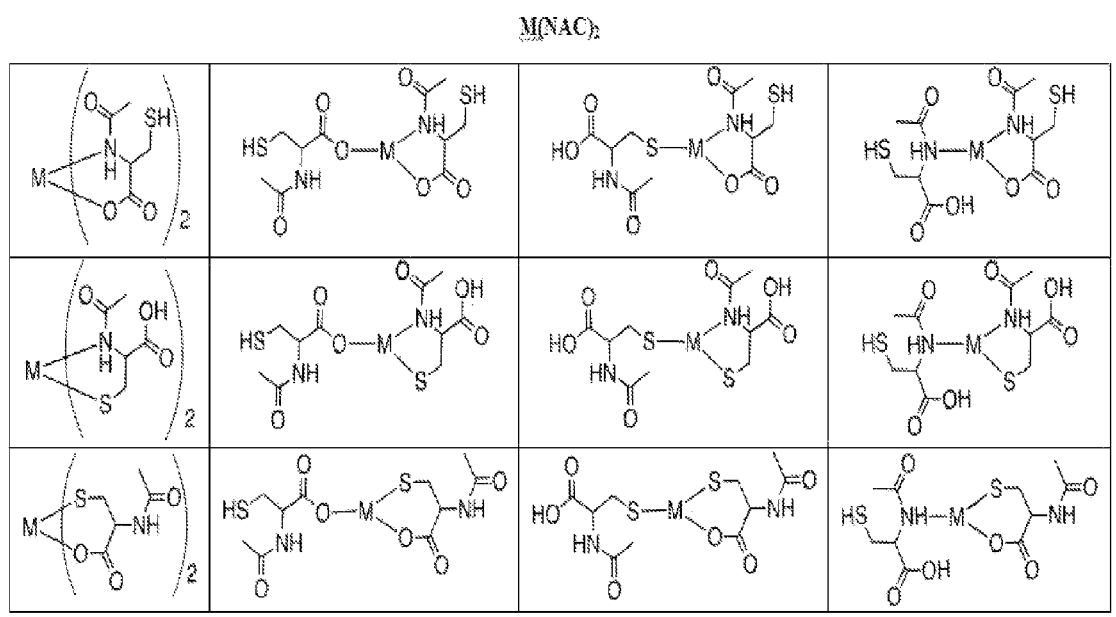
FIG. 2 is an NAC chelate with a mineral, where the molar ratio is 2:1.
Figure 3:
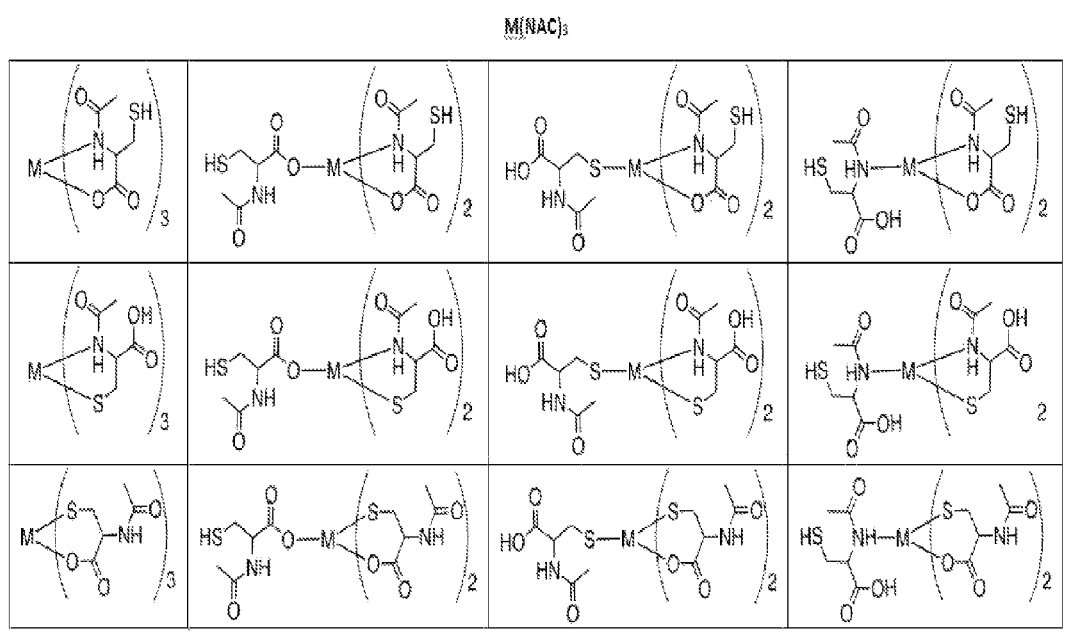
FIG. 3 is an NAC chelate with a mineral, where the molar ratio is 3:1.
Figure 4:
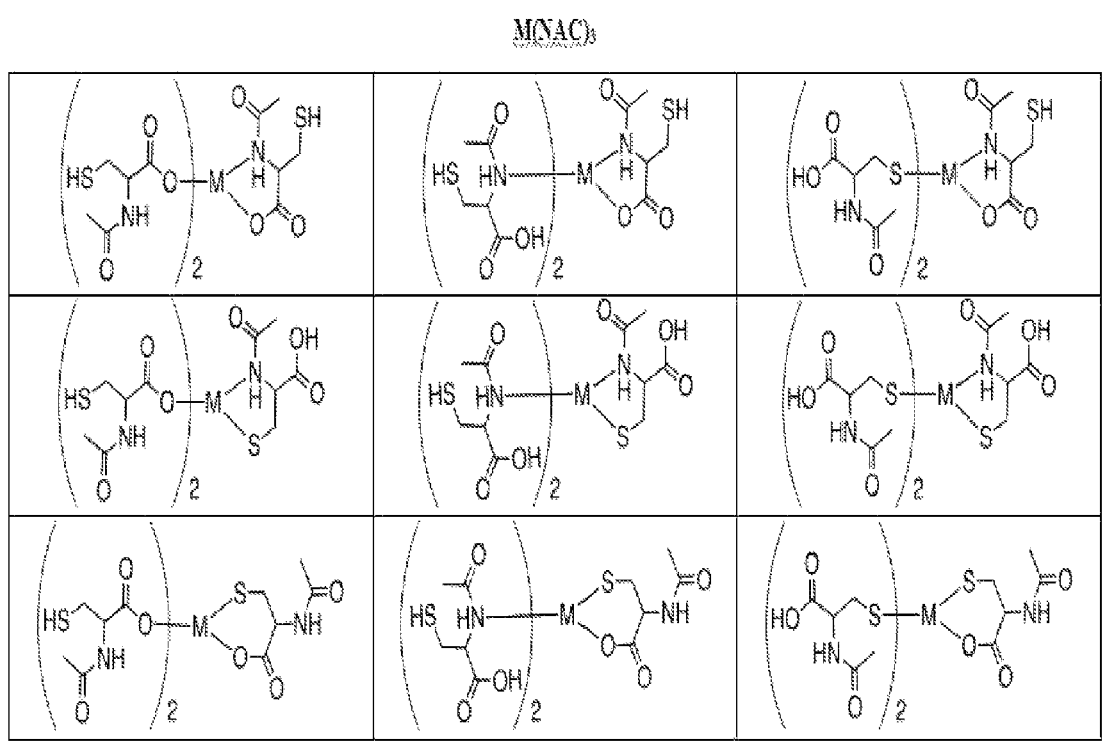
FIG. 4 is an NAC chelate with a mineral, where the molar ratio is 3:1.
Figure 5:
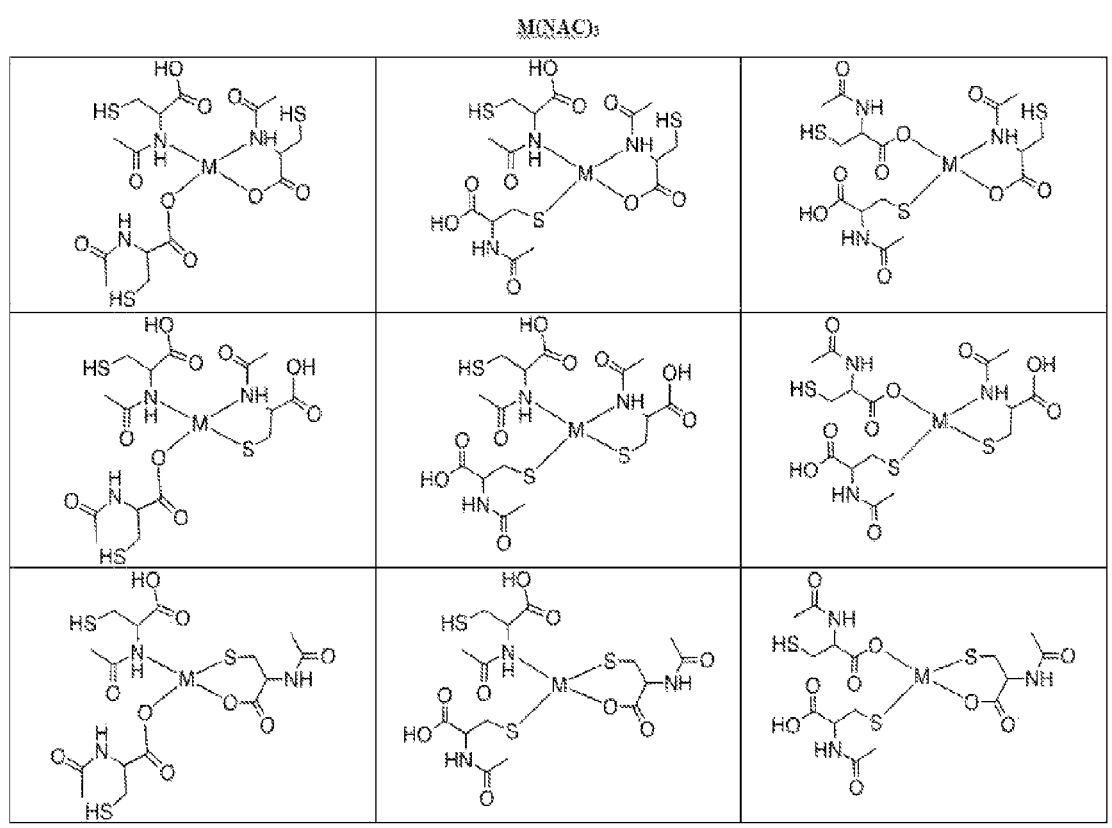
FIG. 5 is an NAC chelate with a mineral, where the molar ratio is 3:1.
Figure 6:
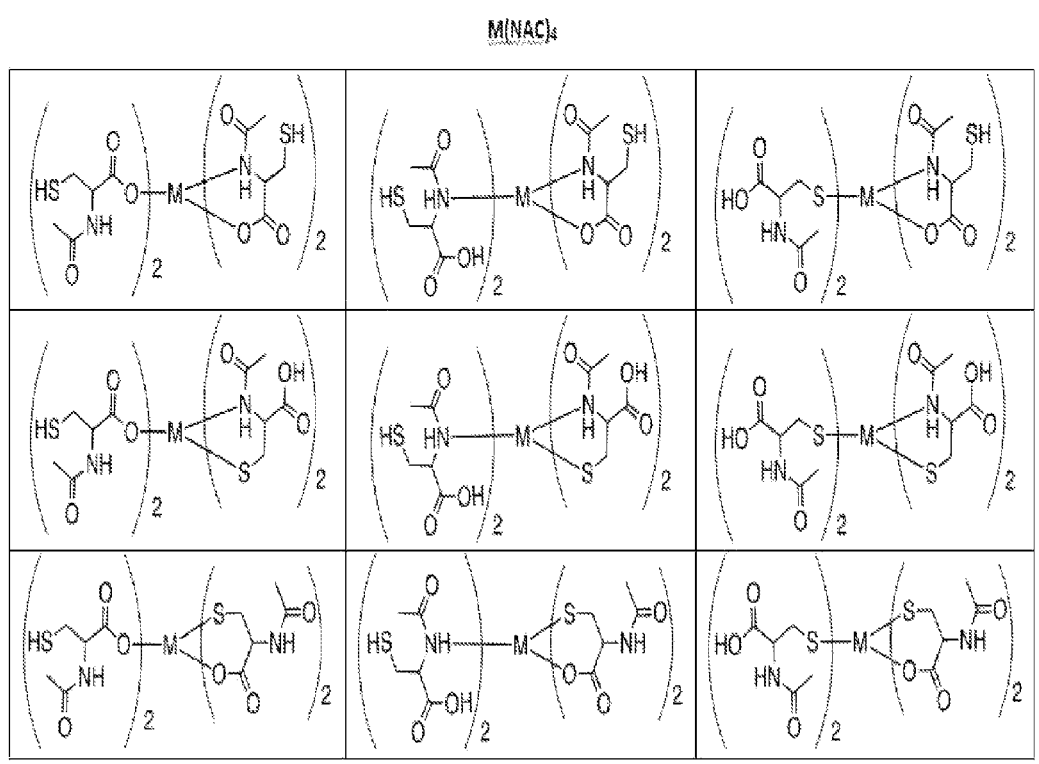
FIG. 6 is an NAC chelate with a mineral, where the molar ratio is 4:1.
Figure 7:
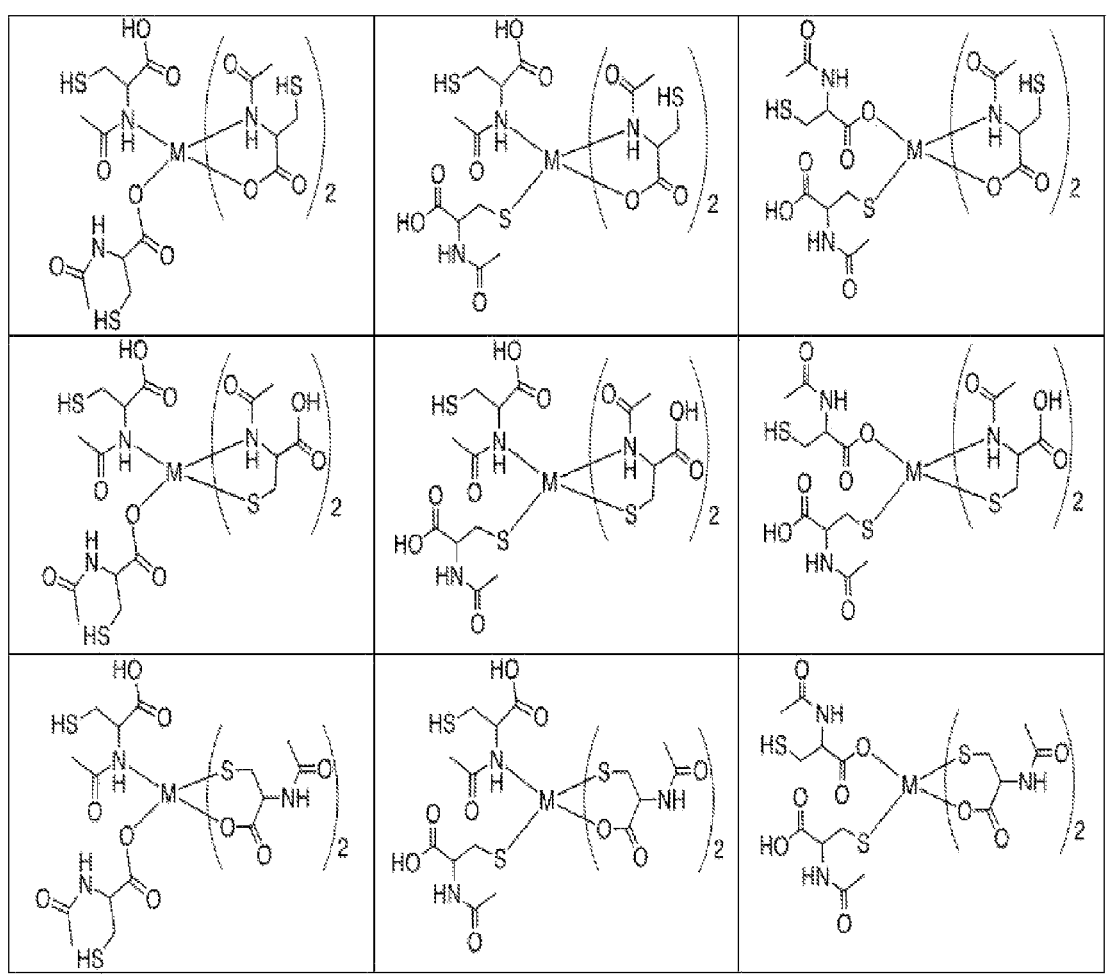
FIG. 7 is an NAC chelate with a mineral, where the molar ratio is 4:1.
Figure 8:
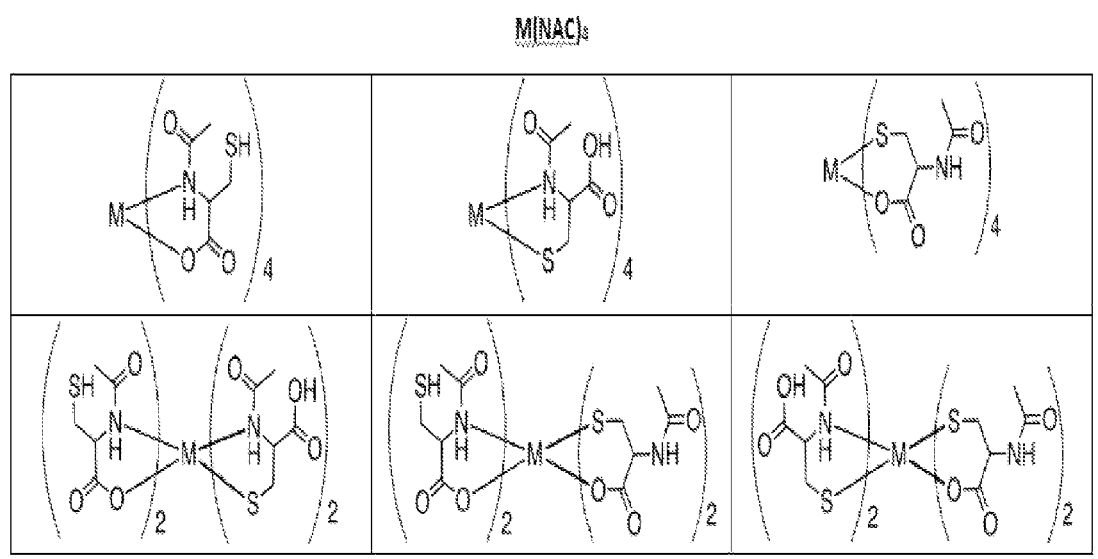
FIG. 8 is an NAC chelate with a mineral, where the molar ratio is 4:1.

FT-IR was used to confirm the existence and bond formation of the NAC chelates with 1 member ring, 2 member rings, 3 member rings, and 4 member rings. FIG. 1 shows the NAC chelate with 1 ring. FIG. 2 shows NAC chelates with 2 member rings. FIG. 3, FIG. 4, and FIG. 5 show the NAC chelate with 3 member rings. FIG. 6, FIG. 7, and FIG. 8 show the NAC chelate with 4 member rings. NAC chelates with 5-member rings were also created; however, the FT-IR method of confirming such structures was unable to confirm how many different formations of NAC chelate with 4 member rings exist.

NAC chelates of Ca, Mg, Zn, and Fe were confirmed to all have a 5-member ring structure, which indicated amino acid chelates formed.

It should be emphasized that the embodiments described herein are merely possible examples of implementations, merely set forth for a clear understanding of the principles of the present disclosure. Many variations and modifications may be made to the described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

One should note that conditional language, such as, among others, "can," "could," "might," or "may," unless specifically stated otherwise, or otherwise understood within the context as used, is generally intended to convey that certain embodiments include, while alternative embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment. Unless stated otherwise, it should not be assumed that multiple features, embodiments, solutions, or elements address the same or related problems or needs.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

The invention claimed is:

1. A nutritional supplement for a human, the supplement comprising a chelate consisting of at least one N-acetyl-L-cysteine ligand bonded to a metal forming a chelate ring, wherein the N-actyl-L-cysteine has the molecular formula $C_5H_7NO_3S$, wherein the metal is selected from the group consisting of magnesium, zinc, or copper.

2. The nutritional supplement of claim 1, wherein the N-acetyl-L-cysteine ligand to metal molar ratio is from 1:1 to 4:1.

3. A nutritional supplement for a human, the supplement comprising a chelate consisting of at least one N-acetyl-L-cysteine ligand bonded to a metal forming a chelate ring, wherein the N-actyl-L-cysteine has the molecular formula $C_5H_7NO_3S$, wherein the metal is selected from the group consisting of manganese, molybdenum, chromium, or selenium.

4. The nutritional supplement of claim 1, wherein the metal is provided by a member selected from the group consisting of ions, elemental, oxides, hydroxides, carbonates, bicarbonates, sulfates, nitrates, chlorides, phosphates, citrates, lactates, amino acid salts, gluconates, and fumurates, and combinations thereof.

5. The nutritional supplement of claim 1, wherein the N-acetyl-L-cysteine ligand is N-acetyl-L-cysteine amide or N-acetyl-L-cysteine ester.

6. A nutritional supplement for a human, the supplement comprising a chelate consisting of at least one N-acetyl-L-cysteine ligand bonded to iron forming a chelate ring, wherein the N-actyl-L-cysteine has the molecular formula $C_5H_7NO_3S$, and wherein the N-acetyl-L-cysteine ligand to iron molar ratio is from 1:1 to 4:1.

7. A method of treating a human for one or more of oxidative stress, cardiovascular disease, cerebrovascular disease, neurodegenerative diseases, Alzheimer's disease, ADHD, improved vision, bipolar disorder, schizophrenia, autism, dementia, and HIV in a human comprising administering an effective amount of a pharmaceutically acceptable composition according to any of claims 1, 3, or 6.

8. The method of claim 7, wherein the chelate is N-acetyl-L-cysteine magnesium.

9. The method of claim 7, wherein the chelate is N-acetyl-L-cysteine zinc.

10. The method of claim 7, wherein the chelate is N-acetyl-L-cysteine iron.

11. The method of claim 7, wherein the chelate is N-acetyl-L-cysteine copper.

12. The nutritional supplement of claim 1, wherein the N-acetyl-L-cysteine ligand to magnesium molar ratio is from 3:1 to 4:1.

13. The nutritional supplement of claim 1, wherein the N-acetyl-L-cysteine ligand to copper molar ratio is from 1:1.

14. The nutritional supplement of claim 1, wherein the N-acetyl-L-cysteine ligand is bonded to magnesium forming an N-acetyl-L-cysteine magnesium chelate, wherein N-acetyl-L-cysteine magnesium chelate is $Mg(C_5H_7NO_3S)_2$.

15. The nutritional supplement of claim 1, wherein the N-acetyl-L-cysteine ligand is bonded to magnesium forming an N-acetyl-L-cysteine magnesium chelate, wherein N-acetyl-L-cysteine magnesium chelate is $Mg(C_5H_7NO_3S)_3$.

16. The nutritional supplement of claim 1, wherein the N-acetyl-L-cysteine ligand is bonded to magnesium forming an N-acetyl-L-cysteine magnesium chelate, wherein N-acetyl-L-cysteine magnesium chelate is $Mg(C_5H_7NO_3S)_4$.

17. The nutritional supplement of claim 1, wherein the N-acetyl-L-cysteine ligand is bonded to iron forming an N-acetyl-L-cysteine magnesium chelate, wherein N-acetyl-L-cysteine iron chelate is $Fe(C_5H_7NO_3S)_2$.

18. The nutritional supplement of claim 1, wherein the N-acetyl-L-cysteine ligand is bonded to iron forming an N-acetyl-L-cysteine iron chelate, wherein N-acetyl-L-cysteine iron chelate is $Fe(C_5H_7NO_3S)_3$.

19. The nutritional supplement of claim 1, wherein the N-acetyl-L-cysteine ligand is bonded to copper forming an N-acetyl-L-cysteine copper chelate, wherein N-acetyl-L-cysteine copper chelate is $Cu(C_5H_7NO_3S)$.

20. The nutritional supplement of claim 1, wherein the nutritional supplement is a tablet or softgel.

* * * * *

UNITED STATES PATENT AND TRADEMARK OFFICE
CERTIFICATE OF CORRECTION

PATENT NO. : 9,062,086 B2
APPLICATION NO. : 14/142683
DATED : June 23, 2015
INVENTOR(S) : Xie et al.

It is certified that error appears in the above-identified patent and that said Letters Patent is hereby corrected as shown below:

In the claims

Column 17 line 43-48 Claim 1 should read:

A nutritional supplement for a human, the supplement comprising a chelate consisting of at least one N-acetyl-L-cysteine ligand bonded to a metal forming a chelate ring, wherein the N-actyl-L-cysteine has the molecular formula C5H7NO3S, wherein the metal is selected from the group consisting of magnesium or copper.

Signed and Sealed this
Twenty-second Day of December, 2015

Michelle K. Lee
*Director of the United States Patent and Trademark Office*